Figure 1:
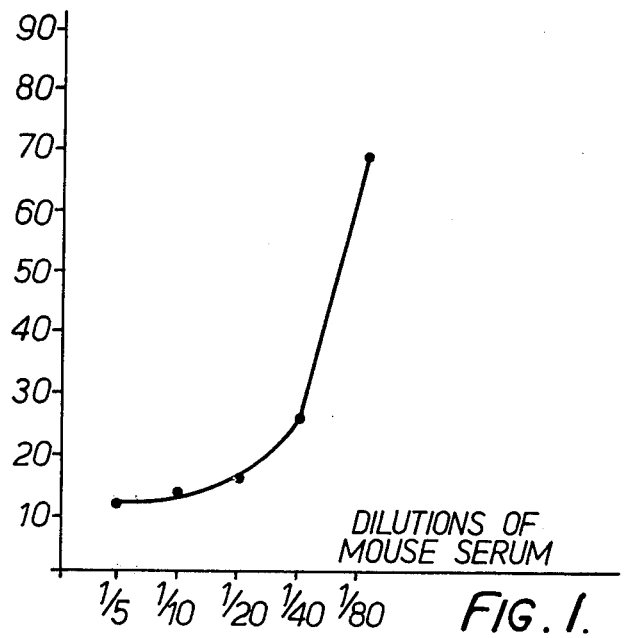

United States Patent [19]
Cambiaso et al.

[11] 4,162,895
[45] Jul. 31, 1979

[54] MOUSE SERUM

[75] Inventors: Cesar L. Cambiaso; Pierre L. Masson, both of Brussels, Belgium

[73] Assignee: Technicon Instruments Corporation, Tarrytown, N.Y.

[21] Appl. No.: 857,537

[22] Filed: Dec. 5, 1977

[30] Foreign Application Priority Data

Dec. 10, 1976 [GB] United Kingdom ............... 51739/76

[51] Int. Cl.² ...................... G01N 33/16; G01N 31/14
[52] U.S. Cl. ................................... 435/7 B; 252/408; 23/915; 424/12; 23/230 B
[58] Field of Search ........................ 23/230 B; 424/12; 252/408; 195/103.5 A; 422/915

[56] References Cited

U.S. PATENT DOCUMENTS

| 3,594,466 | 7/1971 | Guffroy | 424/12 |
|---|---|---|---|
| 3,658,982 | 4/1972 | Reiss | 424/12 |
| 3,689,632 | 9/1972 | Mizushima | 424/12 |
| 3,857,931 | 12/1974 | Hager | 424/12 |
| 4,062,935 | 12/1977 | Masson | 424/12 |

FOREIGN PATENT DOCUMENTS 951242 7/1974 Canada ..................... 424/12

Primary Examiner—Sidney Marantz
Attorney, Agent, or Firm—S. P. Tedesco

[57] ABSTRACT

In the analysis of liquids, particularly biological liquids such as serum or urine, mouse serum or a component of mouse serum is used as a reagent. The reagent has the ability to combine with antibody:antigen complexes (but not free antibody or antigen) and to combine with IgG and IgM. It differs markedly from human C1q in that it remains active at high pH and in the presence of certain substances known to destroy human C1q. It is a very broadly applicable reagent in immunoassays, and particularly useful in techniques involving agglutination latex particles.

25 Claims, 3 Drawing Figures

MOUSE SERUM

This invention relates to the analysis of liquids, particularly but not exclusively biological fluids such as serum or urine, for the presence therein of antigens, antibodies and antibody:antigen complexes. In this specification, the symbols "Ag", "Ab" and "Ab:Ag" are used respectively for antigen(s) (by which term we include haptens and other substances which can be bound by antibodies or similar binding proteins), antibody(ies) (including similar binding proteins) and antibody:antigen complex(es).

As is well known, it is important to be able to analyse liquids, particularly biological liquids, for Ab, Ag or Ab:Ag therein. For example, many diseases are characterised by the presence of Ab:Ag, and hence their detection and characterisation can provide information of value in the diagnosis of disease. There are a number of techniques known for detecting and quantifying Ag, Ab and Ab:Ag and particularly for determining the nature and amount of Ag present. These quantification techniques are called "immunoassay" procedures.

We have now found that, surprisingly, whole mouse serum contains an active fraction which is an extremely useful reagent in assays for Ab, Ag and Ab:Ag, and its use can for example simplify and render more accurate immunoassay techniques. In particular, we have found that mouse serum contains a fraction which has the ability to combine with Ab:Ag but not with free Ab or Ag. Further, the active fraction causes the agglutination of various immunoglobulins when heat aggregated, latex bound or modified in a similar way.

According to the invention, there is provided a method of analysing a liquid sample for Ab, Ag or Ab:Ag therein, which includes the step of adding to the sample, before or after adding other reagents, the active fraction of mouse serum to bind with Ab:Ag present in, or generated in, the sample.

The active fraction of mouse serum which is used in the present invention is a euglobulin. In some of its properties, it closely resembles human C1q. For example, it combines with Ab:Ag but not with free Ab or Ag; it has a sedimentation constant of 10S; it selectively binds with IgG and IgM but not IgA; it agglutinates latex particles coated with IgG or IgM; and it attaches to the same portion of the Fc chain of IgG as does human C1q. In other respects, however, it has quite different properties from human C1q. For example, it remains active at high pH's, e.g. above 8 and, particularly, above 9.2 (at which pH human C1q is inactive); its activity is not destroyed by 0.1M putrescine or by 0.1M hydrazine.

The active fraction of mouse serum is obtained by separation techniques commonly used in the art, for example, in a manner similar to that in which human C1q is obtained from human serum. Thus, for example, if whole mouse serum is passed through a chromatographic column of aminated agarose having human IgG coupled thereto (by glutaraldehyde), the active fraction of the mouse serum will be absorbed. The fraction can then be eluted using 1M sodium chloride solution. The eluant can be dialysed (to separate the sodium chloride) and finally the active fraction taken up in GBS (0.1M glycine - HCl buffer, pH 9.2).

It is unexpected that mouse serum should contain an active fraction having different properties from human C1q, since human serum and the sera of other animals such as horse, goat and rabbit do not appear to possess such a fraction. The difference in properties between the active fraction of mouse serum and human C1q provide substantial advantages in the assay of human sera (to be hereinafter described).

Insofar as the active fraction of mouse serum resembles human C1q, it can be used in analyses in the same way as human C1q. The use of human C1q in assays is described in our British specification no. 21619/75 to which reference should be made for further details.

An important advantage of using the active fraction of mouse serum in analyses, instead of human C1q, is that whole mouse serum can be used; it is not essential, or even usually necessary, to separate out the active fraction. By contrast, in most analyses where human C1q is used as a reagent, it is not possible to use whole human serum: the C1q must be separated out. The avoidance of such a separation step is highly advantageous. Furthermore, mouse serum is far more readily available than is separated human C1q, and is therefore a more economic reagent to use.

Among the preferred methods of analysis of the present invention are the following:

(1) A method of assaying an Ab or Ag in a liquid, which comprises
   (a) adding to the liquid an Ag or Ab which is specific to the Ab or Ag, respectively, under assay in the liquid to form an Ab:Ag therewith;
   (b) adding to the mixture from step (a) a known amount of the Ab or Ag to be determined, which amount carries an identifying label
   (c) adding to the mixture formed in step (b) the said active fraction in an amount at least sufficient to bind with all the Ab:Ag in the mixture; and
   (d) measuring the amount of labelled Ab or Ag remaining free in the mixture or bound to the said active fraction.

The identifying label may, for example, be an enzyme or co-enzyme such that the activity of the enzyme or co-enzyme is inhibited upon binding of the Ab:Ag or labelled Ab:Ag to the said active fraction, and the amount of free labelled Ab or Ag is determined by measuring the enzyme or co-enzyme activity of the mixture without first removing the Ab:Ag bound to the said active fraction. Suitable such enzymes include catalase and amylase.

Alternatively, in the above method (1), the Ab:Ag bound to the said active fraction is removed from the mixture, and the amount of labelled Ag or Ab remaining in the mixture is then measured.

(2) A method of determining the presence in, or absence from, a liquid of an Ab:Ag, which comprises adding to the liquid the said active fraction and a material which is caused to agglutinate on contact with any of the said active fraction not bound to Ab:Ag, and detecting whether or not agglutination of the material occurs.

Preferably, the material comprises inert carrier particles such as latex, having a coating of an immunoglobulin (IgG or IgM).

(3) A method of detecting the presence of a particular Ab or Ag in a liquid, which comprises adding to the liquid an Ag or Ab which is specific to the particular Ab or Ag whose presence is to be determined, to form Ab:Ag with any of said particular Ab or Ag present; and determining the presence or absence of such Ab:Ag by the method (2) above.

(4) A method of analysing a liquid for Ab:Ag complexes therein, which comprises adding to the liquid a known amount of inert carrier particles coated with IgG or IgM, the particles being agglutinatable on contact with the Ab:Ag complex and on contact with the said active fraction; and adding also to the liquid a quantity of the said active fraction; incubating the mixture so formed; counting the number of unagglutinated particles; and calculating thereby the amount of complex in the liquid. The Ab:Ag in the liquid may have been formed by adding to a liquid containing an Ab or Ag to be assayed, a respective Ag or Ab to form a liquid containing the Ab:Ag, the amount of Ab or Ag under assay being derived from the calculated amount of complex.

(5) A method of analysing a liquid for Ag therein which comprises adding to the liquid a known amount of inert carrier particles coated with Ab to said Ag, the particles being agglutinatable on contact with the Ag and on contact with said active fraction, and adding also to the liquid a quantity of said active fraction; incubating the mixture so formed; counting the number of unagglutinated particles; and calculating thereby the amount of Ag in the sample.

(6) A method of analysing a liquid for Ab therein which comprises adding to the liquid a known amount of inert carrier particles coated with Ag to said Ab, the particles being agglutinatable on contact with the Ag and on contact with said active fraction, and adding also to the liquid a quantity of said active fraction; incubating the mixture so formed; counting the number of unagglutinated particles; and calculating thereby the amount of Ab in the sample.

In both methods (5) and (6) the inert carrier particles are preferably latex particles, whose size is preferably about 0.8 to 1.1 microns.

In the analysis of human serum samples using human Clq, account has to be taken of the fact that the serum itself will contain human complement Cl. To avoid interference from the resulting Clq in the analysis of the serum using human Clq as an added reagent, the serum must first be treated to inactivate the native Clq. One technique for this is to heat the serum to about 56° C. and keep it at that temperature for about 30 minutes. However, whilst this treatment inactivates the native Clq in the serum, it also has other effects on the serum which can render the subsequent analysis less accurate.

By using mouse serum (or the separated active fraction thereof) as a reagent according to the present invention, the necessity for this heating step when assaying human sera may be avoided by, for example, conducting the analysis at a high pH, e.g. 9.2. At high pH's, any human Clq in the serum umder test is inactive, whereas the mouse serum reagent remains active. Alternatively, the analysis could be effected in the presence of 0.1M hydrazine or 0.1M putrescine, under which conditions human Clq is inactive but mouse serum is not. These properties of mouse serum thus enable the avoidance of interference from native Clq.

It will be appreciated that this is a highly advantageous feature of using mouse serum (or its active fraction) in the analysis of human sera.

The methods of the invention may advantageously be effected by continuous flow techniques, which are known in the art. In continuous flow analyses, mouse serum can be more conveniently used as a reagent than human Clq since the manifold and incubation system for human rheumatoid factor is suitable also for use with mouse serum but not with human Clq.

We prefer to use serum from mice of the BALBc or DBA2 strains. In use, the mouse serum will normally be diluted from about 1/25 to about 1/75 (although the precise dilution will depend on the particular use intended), using as a solvent, for example, 0.1M glycine buffer adjusted to pH 9.2 with caustic soda, and containing 0.15M sodium chloride.

In order that the invention may be more fully understood, the following Examples are given by way of illustration only.

EXAMPLE 1

Mouse serum will cause the agglutination of IgG-coated latex particles, and also of heat-aggregated IgG, the active fraction of the mouse serum reacting preferentially with heat-aggregated IgG.

Thus, if a quantity of mouse serum is mixed with IgG-coated latex (latex-IgG) particles, aggregation of the particles will occur. If heat-aggregated IgG is now added, the active fraction from the mouse serum will be taken up in agglutinating the heat-aggregated IgG until, eventually, there is no remaining aggregation of the latex. The activity of the mouse serum can be expressed in terms of the amount of heat-aggregated IgG necessary to prevent any aggregation of the latex. Similarly, the activity of human serum can be expressed in terms of the amount of heat-aggregated IgG that would have been necessary to prevent to the same extent the agglutination of latex IgG. By making tests on sera from 50 healthy blood donors, this activity has been found to be at most 10µg/ml of equivalents of heat-aggregated IgG (EHAIgG).

We have also measured the activity of human sera from patients with multiple sclerosis (75 patients) and from patients with thyroid disorders (58 patients). Among the patients with multiple sclerosis, 30% had sera activities above 10µg/ml (EHAIgG) and among the patients with thyroid disorders, 65.5% had sera activities above 10µg/ml (EHAIgG). It will be appreciated that the higher activity indicates the presence in the sera of immune complexes (these being absent or substantially absent from the healthy patients).

Mouse serum has a greater avidity for some immune complexes than for others. RF likewise has a varying avidity for immune complexes. We recommend, therefore, that in tests on human sera for the presence of immune complexes, both mouse serum and RF tests be run in parallel. For information concerning the use of RF, reference should be made to our British application no. 21619/75.

EXAMPLE 2

(1) Preparation of mouse serum

The mouse serum is diluted in GBS (0.1 M glycine-HCl buffer, pH 9.2, containing 0.17 M NaCl). The dilution ranges from 1/50 to 1/80 depending on the batch of mouse serum.

(2) Preparation of patient's sera before analysis

A volume of serum of 50 µl is added to 170 µl of GBS containing 50 mM EDTA (pH 9.2) and then reduced by 1.5 mM dithiotreitol (15 µl) for 15 minutes at 37° C. The sample is then reoxidized by 15 µl of 0.2% $H_2O_2$. This reduction of the serum sample aimed to eliminate any agglutinating factor which could interfere with the inhibition process. The reoxidation is necessary to inactivate the residual dithiothreitol which could destroy the agglutinating factor of the mouse serum. It is to be noted that whilst this treatment will to a limited extent inactivate endogenous Clq in the sera, its main purpose is to inactivate other agglutinating factors such as RF. Full inactivation of Clq is achieved by conducting the analyses at a pH of 9.2.

(3) Preparation of latex

Polystyrene particles (0.794 μ) from Dow Chemical Company (Indianapolis, Ind.) are coated with human IgG as follows. To 400 μl of 5-fold diluted GBS, are added 25 μl of a 1% (w/v) solution of IgG, 150 μl of 1% (w/v) solution of human serum albumin (Behringwerke, Marburg West Germany), and then 50 μl of the 10% (w/v) latex suspension. After vortexing for a few seconds and incubating at room temperature for 45 minutes, the suspensions are centrifuged at 10,000 rev/min for 5 minutes, the particles are washed once with 1 ml diluted GBS, and finally resuspended in 10 ml. GBS containing 1% (w/v) bovine serum albumin.

(4) Automated Analysis

The same volumes (70 μl) of serum sample, mouse serum and latex suspension, as described above, are aspirated together into the manifold. The incubation time is 10 minutes. After incubation, the mixture is diluted 2000 times automatically with GBS containing 0.1% Tween 20, and the non-agglutinated latex particles were then counted in a Technicon optical cell counter (Autocounter) with a lower and upper threshold. The run requires a 2000-fold dilution of the latex suspension to restrict the count to a maximum of 4000 particles/sec.

(5) Results

Serial two-fold dilutions of mouse serum give the agglutination curve of FIG. 1. The ordinates represent the height of the peaks on the recorder. The height is directly proportional to the number of free (non-agglutinated) particles.

Figure 2:
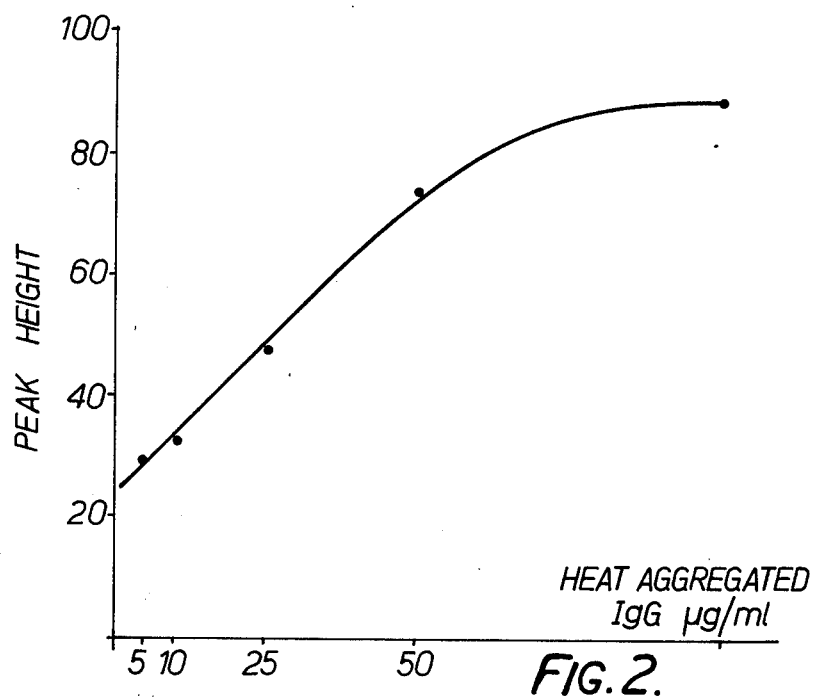

Standard curve (FIG. 2) is determined with a range of concentration, of heat-aggregated IgG in GBS. The results are expressed in μg/ml of equivalents of heat-aggregated human IgG. The latter are prepared by DEAE-cellulose chromatography from a pool of human sera and aggregated by heating at 63° C. for 30 minutes.

Figure 3:
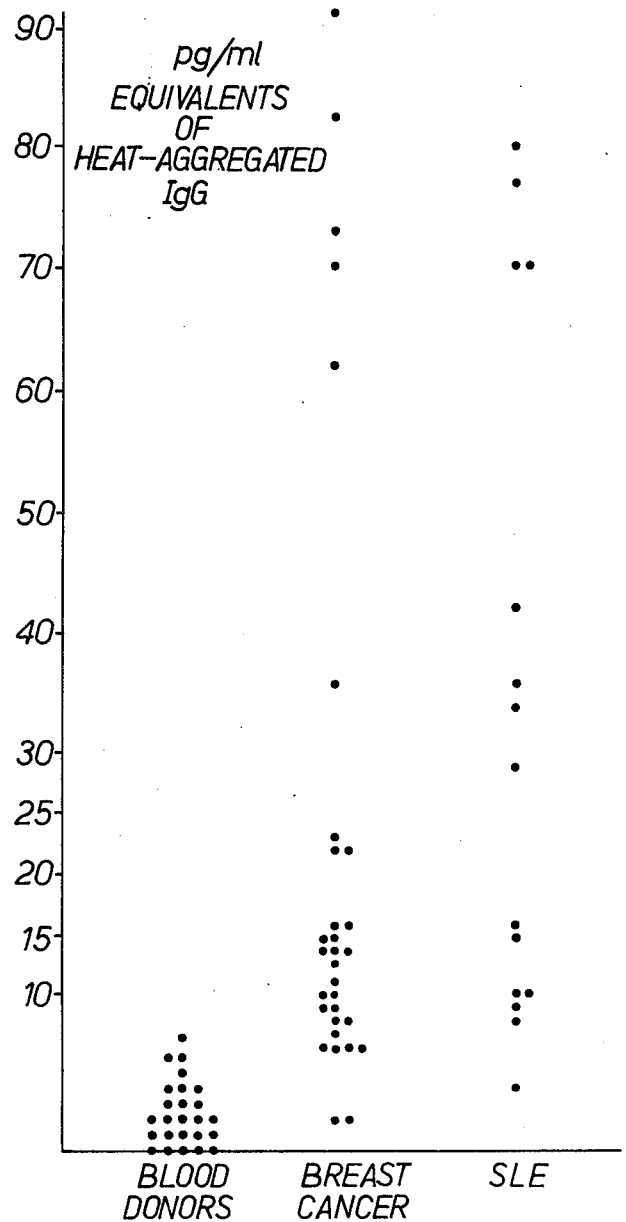

FIG. 3 represents the results of the inhibition of mouse serum by sera from healthy blood donors, patients with breast cancer, and patients with systemic lupus erythematosus (SLE). The upper limit for the normal values is 7 μg/ml of equivalents of heat-aggregated IgG.

What we claim is:

1. A method of analysing a liquid for the presence therein of Ab, Ag or Ab:Ag, which includes the step of adding to the liquid, before or after adding other reagents, the active fraction of whole mouse serum, to bind with Ab:Ag present in or generated in the sample.

2. A method according to claim 1, wherein the said active fraction is added in the form of whole mouse serum.

3. A method according to claim 1 for detecting the presence of a particular Ab or Ag in the liquid, which comprises adding to the liquid an Ag or Ab which is specific to the particular Ab or Ag whose presence is to be determined, to form Ab:Ag with any of said particular Ab or Ag present; and determining the presence or absence of such Ab:Ag.

4. A method according to claim 1 for analysing a liquid for Ab therein which comprises adding to the liquid a known amount of inert carrier particles coated with Ag to said Ab, the particles being agglutinable to contact with the Ag and on contact with said active fraction, and adding also to the liquid a quantity of said active fraction; incubating the mixture so formed; counting the number of unagglutinated particles; and calculating thereby the amount of Ab in the sample.

5. A method according to claim 1, wherein the liquid is a biological fluid of human origin.

6. A method according to claim 1, wherein the said active fraction binds with Ab:Ag in the presence of 0.1 M putrescine or 0.1 M hydrazine.

7. A method according to claim 1, which is effected on a continuous flow basis.

8. A method according to claim 1 for determining the presence in, or absence from, the liquid of an Ab:Ag, which comprises adding to the liquid a material which is caused to agglutinate on contact with any of the said active fraction not bound to Ab:Ag, and detecting whether or not agglutination of the material occurs.

9. A method according to claim 8 wherein the material comprises an IgG or IgM coating on inert carrier particles.

10. A method according to claim 9 wherein the particles comprise latex.

11. A method according to claim 10, wherein the size of the particles is about 0.8 to 1.1 microns.

12. A method according to claim 1 for analysing a liquid for Ab:Ag complexes therein, which comprises adding to the liquid a known amount of inert carrier particles coated with IgG or IgM, the particles being agglutinatable on contact with the Ab:Ag complex and on contact with the said active fraction; and adding also to the liquid a quantity of the said active fraction; incubating the mixture so formed; counting the number of unagglutinated particles; and calculating thereby the amount of complex in the liquid.

13. A method according to claim 12, wherein the Ab:Ag in the liquid has been formed by adding to a liquid containing an Ab or Ag to be assayed, a respective Ag or Ab to form a liquid containing said Ab:Ag, and wherein the amount of Ab or Ag under assay is derived from the said calculated amount of complex.

14. A method according to claim 12, wherein the said inert carrier particles are latex particles.

15. A method according to claim 14, wherein the size of the particles is about 0.8 to 1.1 microns.

16. A method according to claim 1 for analysing a liquid for Ag therein which comprises adding to the liquid a known amount of inert carrier particles coated with Ab to said Ag, the particles being agglutinatable on contact with the Ag and on contact with said active fraction, and adding also to the liquid a quantity of said active fraction; incubating the mixture so formed; counting the number of unagglutinated particles; and calculating thereby the amount of Ag in the sample.

17. A method according to claim 16, wherein said inert carrier particles are latex particles.

18. A method according to claim 1, wherein the said active fraction binds with Ab:Ag at a pH of at least 8.

19. A method according to claim 18 wherein the pH is at least 9.2.

20. A method for assaying an Ab or Ag in a liquid, which comprises:

(a) adding to the liquid an Ag or Ab which is specific to the Ab or Ag, respectively, under assay in the liquid to form an Ab:Ag therewith;

(b) adding to the mixture from step (a) a known amount of the Ab or Ag to be determined, which amount carries an identifying label;

(c) adding to the mixture formed in step (b) the active fraction of whole mouse serum in an amount at least sufficient to bind with all the Ab:Ag in the mixture; and (d) measuring the amount of labelled Ab or Ag remaining free in the mixture or bound to the said active fraction.

21. A method according to claim 20, wherein the said active fraction is added in the form of whole mouse serum.

22. A method according to claim 20 wherein the Ab:Ag bound to the said active fraction is removed from the mixture, and the amount of labelled Ag or Ab remaining in the mixture is then measured.

23. A method according to claim 20, wherein the liquid is a biological fluid of human origin.

24. A method according to claim 20 wherein the identifying label is an enzyme or co-enzyme such that the activity of the enzyme or co-enzyme is inhibited upon binding of the Ab:Ag or labelled Ab:Ag to the said active fraction, and the amount of free labelled Ab or Ag is determined by measuring the enzyme or co-enzyme activity of the mixture without first removing the Ab:Ag bound to the said active fraction.

25. A method according to claim 24 wherein the labelled Ab or Ag carries, as the idenfifying label, catalase or amylase.

* * * * *